United States Patent [19]

Lim et al.

[11] 4,374,994

[45] Feb. 22, 1983

[54] PROCESS FOR PREPARATION OF 5-MERCAPTOTETRAZOLYL-1-ACETIC ACID

[75] Inventors: Gary M. F. Lim; Masaki Endo, both of Candiac, Canada

[73] Assignee: Bristol-Myers Company, New York, N.Y.

[21] Appl. No.: 54,743

[22] Filed: Jul. 5, 1979

[51] Int. Cl.³ .............................................. C07D 257/04
[52] U.S. Cl. .................................................... 548/251
[58] Field of Search ................ 548/251, 253, 250, 252

[56] References Cited

PUBLICATIONS

Stolle et al., Siprakt. Chem. [2] 134, pp. 282–309 (1932).
Waudell *Piep. of Thiols,* Ch. 4 "The Chemistry of the Thiol Group", Part I. Patai (ed), pp. 186 & 187, Wiley, N.Y., (1974).

*Primary Examiner*—Donald G. Daus
*Assistant Examiner*—D. B. Springer
*Attorney, Agent, or Firm*—Herbert W. Taylor, Jr.

[57] ABSTRACT

5-Mercaptotetrazolyl-1-acetic acid is prepared by bromination with molecular bromine of tetrazolyl-1-acetic acid to produce 5-bromotetrazolyl-1-acetic acid which is then reacted with thiourea to displace the bromine and, after alkaline hydrolysis, to produce 5-mercaptotetrazolyl-1-acetic acid.

1 Claim, No Drawings

PROCESS FOR PREPARATION OF 5-MERCAPTOTETRAZOLYL-1-ACETIC ACID

BACKGROUND OF THE INVENTION

1. Field of the Invention

This invention provides a new chemical process for the production of 5-mercaptotetrazolyl-1-acetic acid which is used as an intermediate in the chemical production of antibacterial agents, e.g. cephalosporins such as ceforanide.

2. Description of the Prior Art 7-(2-Aminomethylphenylacetamido)-3-(1-carboxymethyltetrazol-5-ylthiomethyl)-3-cephem-4-carboxylic acid is a potent injectable cephalosporin having the generic name ceforanide; it has also been called BL-S786 in the literature. It was described, for example, in U.S. Pat. No. 4,100,346.

5-Mercaptotetrazolyl-1-acetic acid (1-carboxymethyl-5-mercaptotetrazole) is the 3-substituent in quite a few active antibiotics of the cephalosporin class, e.g., ceforanide

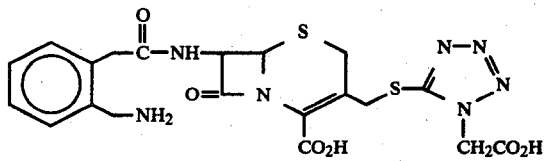

5-Mercaptotetrazolyl-1-acetic acid has been prepared by the following methods:

(a) Butylithiation of 1-methyl-5-mercaptotetrazole followed by reaction with carbon dioxide and acid hydrolysis.

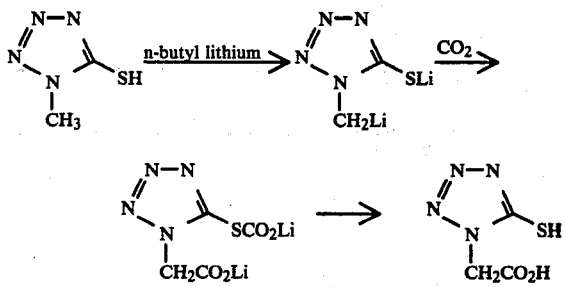

(b) Reacting ethyl glycinate, carbon disulfide and sodium azide.

(c) Reacting 2-carboethoxymethyl isothiocyanate and sodium azide. All are described in detail in U.S. Pat. No. 4,100,346.

Bromination of 1-phenyl-tetrazole in carbon tetrachloride to product 5-bromo-1-phenyltetrazole was reported on page 295 by Stolle et al., J. Prakt. Chem. [2]134, 282–309 (1932). This reaction is apparently not mentioned in the corresponding Chemical Abstracts 26, 5565 (1932) but the page is cited as reference 95 on p. 40–42 of Heterocyclic Compounds, Vol. 8, Tetrazoles, Tetrazines and Purines and Related Ring Systems, Edited by R. C. Elderfield, John Wiley and Sons, Inc., New York (1967).

A brief review of the production of isothiouronium salts from various halides and their conversion to thiols has been provided at pages 186–191 of The Chemistry of the Thiol Group, Part 1, Edited by Saul Patai, John Wiley and Sons, New York (1974). On page 187 therein the cross-reference 94 refers to p. 32–35 of E. E. Reid, Chemistry of Bivalent Sulfur, Vol. 1, Chemical Publishing Co., New York (1958) on the same subject.

U.S. Pat. No. 3,468,874 describes the preparation of tetrazolyl-1-acetic acid in column 10 and of 5-bromo-1-tetrazolylacetic acid in column 16.

5-Mercapto-3-methyl-1,2,4-thiadiazole has been prepared by treatment with thiourea of the corresponding 5-chloro compound (U.S. Pat. No. 3,757,012, columns 5–6) and 2-mercapto-5-methyl-1,3,4-thiadiazole and 2-mercapto-5-hydroxymethyl-1,3,4-thiadiazole have been prepared by treatment with thiourea of the corresponding 5-bromo compounds (U.S. Pat. No. 3,907,786, columns 16 and 23; other preparations are given for other thiols.

SUMMARY OF THE INVENTION

There is provided by the present invention the process for the production of an alkaline solution of 5-mercaptotetrazolyl-1-acetic acid which comprises the consecutive steps of (a) heating a solution of tetrazolyl-1-acetic acid and bromine or its functional equivalent as a brominating agent to product 5-bromotetrazolyl-1-acetic acid, (b) heating said 5-bromotetrazolyl-1-acetic acid in a solvent therefor in the presence of thiourea and then (c) mixing with the resulting mixture a strong base to produce an alkaline solution of 5-mercaptotetrazolyl-1-acetic acid.

There is further provided by the present invention the process for the production of an alkaline solution of 5-mercaptotetrazolyl-1-acetic acid which comprises the consecutive steps of (a) heating, preferably at a temperature between 50° C. and 100° C., a solution in a chlorinated hydrocarbon such as chloroform or carbon tetrachloride of tetrazolyl-1-acetic acid (preferably with enough added acid, preferably acetic acid, to bring the tetrazolyl-1-acetic acid into solution) and a molar excess of bromine or its functional equivalent as a brominating agent, and preferably about twice as many moles of bromine as of tetrazolyl-1-acetic acid, to produce 5-bromotetrazolyl-1-acetic acid, (b) precipitating said 5-bromotetrazolyl-1-acetic acid as a solid by addition of a nonsolvent therefor such as a liquid alkane or a mixture of liquid alkanes, e.g. petroleum ether or heptane, (c) recovering said solid 5-bromotetrazolyl-1-acetic acid and heating it to reflux in a solvent therefor such as a lower aliphatic alcohol and preferably isopropyl alcohol, methanol, ethanol, n-propyl alcohol or n-butyl alcohol in the presence of an amount of thiourea which is preferably about equimolar to the 5-bromotetrazolyl-1-acetic acid and then (d) mixing with the resulting mixture dilute (preferably about 10%) aqueous sodium hydroxide or potassium hydroxide or the alkaline equivalent thereof, preferably with stirring at about room temperature, to produce an alkaline solution of 5-mercaptotetrazolyl-1-acetic acid.

There is further provided by the present invention the process for the production of an alkaline solution of 5-mercaptotetrazolyl-1-acetic acid which comprises the consecutive steps of (a) heating 5-bromotetrazolyl-1-acetic acid to reflux in a solvent therefor in the presence of thiourea and then (b) mixing with the resulting mixture a strong base to produce an alkaline solution of 5-mercaptotetrazolyl-1-acetic acid.

There is further provided by the present invention the process for the production of an alkaline solution of 5-mercaptotetrazolyl-1-acetic acid which comprises the consecutive steps of (a) heating 5-bromotetrazolyl-1-acetic acid to reflux in a solvent therefor such as a lower aliphatic alcohol and preferably isopropyl alcohol, methanol, ethanol, n-propyl alcohol or n-butyl alcohol in the presence of an amount of thiourea which is preferably about equimolar to the 5-bromotetrazolyl-1-acetic acid and then (b) mixing with the resulting mixture dilute (preferably above 10%) aqueous sodium hydroxide or potassium hydroxide or the alkaline equivalent thereof, preferably with stirring at about room temperature, to produce an alkaline solution of 5-mercaptotetrazolyl-1-acetic acid.

There is further provided by the present invention the process for the production of 5-bromotetrazolyl-1-acetic acid which comprises heating, preferably at a temperature between 50° C. and 100° C., a solution in a chlorinated hydrocarbon such as chloroform or carbon tetrachloride of tetrazolyl-1-acetic acid (preferably with enough added acid, preferably acetic acid, to bring the tetrazolyl-1-acetic acid into solution) and a molar excess of bromine or its functional equivalent as a brominating agent, and preferably about twice as many moles of bromine as of tetrazolyl-1-acetic acid, to produce 5-bromotetrazolyl-1-acetic acid.

Bromination of 1-phenyltetrazole in carbon tetrachloride to produce 5-bromo-1-phenyltetrazole has been reported by Stolle et al. (J. prakt. Chem., [2]134, 282–309 (1932), see p. 40 in Robert C. Elderfield "Heterocyclic Compounds" Vol. 8, Chapter 1, John Wiley & Son. Using the reaction conditions described, we failed to brominate tetrazolyl-1-acetic acid at first but later succeeded in brominating the corresponding ethyl ester. We attributed this difference in reactivity to solubilities. We have now brominated tetrazolyl-1-acetic acid in chloroform (or carbon tetrachloride) with added acetic acid to bring the reactant into solution.

The bromination is carried out between the temperature of 50°–100° C. and occurred exclusively at the 5-position of the tetrazole which is unexpected as there are two reactive methylene protons in the molecule also.

The 5-bromotetrazolyl-1-acetic acid is best converted to the 5-mercaptotetrazolyl-1-acetic acid via the corresponding isothiuronium salt in alcohol (e.g. methanol, ethanol, n-propyl alcohol, isopropyl alcohol or n-butyl alcohol).

DESCRIPTION OF THE PREFERRED EMBODIMENT

Example

5-Mercaptotetrazolylacetic acid is prepared by three combined steps. Tetrazolyl-1-acetic acid (U.S. Pat. No. 3,468,874) is first brominated with molecular bromine ($Br_2$) in a chloroform and acetic acid mixture at reflux temperature to give selectively the 5-bromotetrazolyl-1-acetic acid (U.S. Pat. No. 3,468,874). The crude intermediate is precipitated out by diluting with heptane and then collected by filtration and the cake washed with heptane to remove acetic acid.

The 5-bromotetrazolyl-1-acetic acid is then reacted with thiourea in isopropyl alcohol (IPA) at reflux temperature to form the isothiuronium salt. With most of the IPA removed by distillation, the isothiuronium salt is hydrolyzed with dilute sodium hydroxide. After acidification with dilute sulfuric acid and carbon treatment, the product, 5-mercaptotetrazolyl-1-acetic acid, is extracted into ethyl acetate and isolated as disodium salt by addition of two equivalents of sodium 2-ethylhexanoate (2-SEH). The crude product is collected by filtration and recrystallized from methanol-acetone.

CHEMISTRY

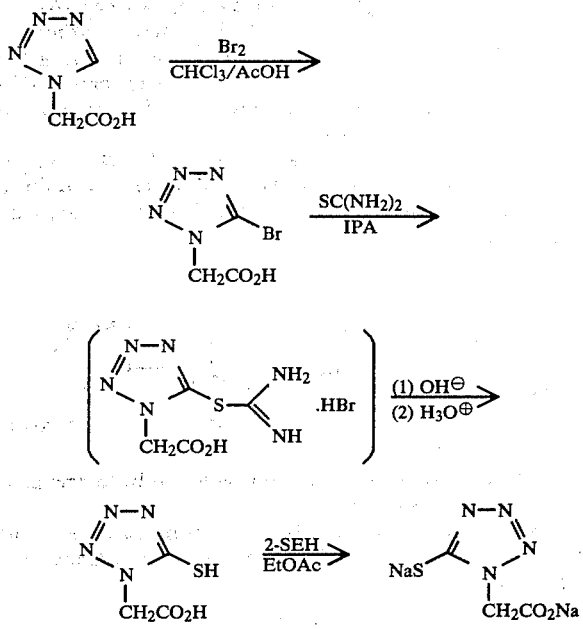

| MATERIALS | | |
|---|---|---|
| | Wt. or Vol. | Moles |
| Tetrazoyl-1-acetic acid | 38.4 g. | 0.3 |
| Bromine | 96.0 g. | 0.6 |
| Glacial Acetic Acid (AcOH) | 231 ml | |
| Chloroform | 540 ml | |
| Heptane | 400 ml | |
| Acetone | 150 ml | |
| Thiourea [$SC(NH_2)_2$] | 22.8 g. | 0.3 |
| Isopropyl Alcohol (IPA) | 600 ml | |
| Sodium Hydroxide (10% aqueous) | 250 ml | |
| Sulfuric Acid (30% aqueous) | as needed | |
| Activated Charcoal ("Darco KB") | 4 g | |
| Ethyl Acetate (EtoAc) | 1300 ml | |
| Sodium 2-ethylhexanoate (2-SEH) | 89.64 g | 0.54 |
| Sodium Chloride | as needed | |
| Diatomaceous Earth ("CELITE") | as needed | |
| Anhydrous Sodium Sulfate | as needed | |

PROCEDURE

1. Equip a 2 L 3-neck flask fitted with a mechanical stirrer, a dropping funnel and a condenser.

2. Place 38.4 g tetrazolyl-1-acetic acid, 231 ml glacial acetic acid and 490 ml chloroform in the flask and bring to reflux.

3. Introduce slowly a solution of 96.0 g. bromine in 50 ml chloroform over 10 min[1] and reflux for 12 h[2].

4. Cool the reaction mixture to room temperature and add 50 ml acetone[3].

5. Add 300 ml heptane after precipitation starts taking place and cool to 0° C. for one-half hour under vigorous agitation.

6. Collect the compound by filtration and wash with 100 ml heptane.

7. Transfer the wet compound together with 22.8 g thiourea and 600 ml isopropyl alcohol to a 1 L 3-neck flask fitted with a condenser, a mechanical stirrer and nitrogen inlet and outlet tubes.

8. Reflux for 2 hours[4].

9. Concentrate the reaction mixture to minimum volume for stirring or when it becomes too viscous for stirring.

10. Add 250 ml 10% aqueous sodium hydroxide solution[5] and stir at room temperature for one-half hour.

11. Acidify with 30% sulfuric acid to pH 1.0 and treat with 4 g of "Darco KB" for 15 minutes.

12. Filter through a bed of "Celite" and wash the filter bed with 50 ml water.

13. Saturate the combined filtrate and wash water with sodium chloride and extract three times with ethyl acetate[6] (500 ml, 300 ml and 200 ml respectively).

14. Dry the ethyl acetate phase over anhydrous sodium sulfate and concentrate to one-half of its volume.

15. Add the ethyl acetate solution dropwise to an anhydrous solution of 89.64 g 2-ethylhexanoic acid sodium salt in 300 ml ethyl acetate under ice cooling[7] and vigorous agitation and stir at room temperature for an additional two hours.

16. Collect the cake by filtration and wash it well with 100 ml acetone. Yield, 50.7 g (83%) of crude disodium salt of 5-mercapto-tetrazolyl-1-acetic acid. After recrystallization[8] from methanol-acetone, overall yield of disodium salt from tetrazolyl-1-acetic acid is 68–70%.

17. Check purity by HPLC using internal standard.

NOTES:
1. Slightly exothermic when bromine is added.
2. Check the termination of reaction with NMR [used $d_6$ acetone as solvent methylene protons shifted from 5.50 (S) to 5.58 ppm and disappearance of proton at 9.33 ppm (S)].
3. The bromine color will be discharged in 10–15 minutes after adding acetone and then precipitation follows shortly after decolorization.
4. Precipitation may take place and the reaction can be monitored with NMR spectrascopy. $d_6$-Acetone as solvent, disappearance of peak at 5.88 ppm.
5. Check the pH of reaction mixture (should be 13) and add more base if necessary.
6. Make sure that the pH is 1.0 before extraction.
7. Gum might form; however, it will gradually solidify. This problem could be prevented by slow addition.
8. The crude salt can be purified by recrystallization from methanol-acetone as follows:
    Dissolve the crude salt in methanol (as a 10% solution) and filter through "Celite" to remove cloudy, insoluble materials. Concentrate the methanol solution until precipitation takes place, then dilute with acetone. After crystallization is complete collect by filtration and dry.

Method for the determination of 1-carboxymethyl-5-mercaptotetrazole (CPD I) in reaction mixtures.

SUMMARY

The amount of CPD I in crude reaction mixtures is determined by HPLC. Quantitation is accomplished by means of an internal standard (CPD II) and comparison to a CPD I reference standard solution.

EQUIPMENT AND REAGENTS

Column: Waters Micro Bondapack $C_{18}$ column (30 cm×3.9 mm I.D.).
Mobile Phase: 20% MeOH, 80% Water plus 0.005 M Pica reagent.
Flow rate: 60 ml/h.
Detector: U.V. fixed wave-length 254 mm Atc 0.16.
Recorded: 1 mu full span. 0.5 cm/min.
Internal standard: 1-Methyl-5-mercaptotetrazole (CPD II).
Reference standard: Purified 1-carboxymethyl-5-mercaptotetrazole (CPD I).
Injector: Rheodyne loop injector, sample size 30 microliter.
Pump: Varian 8500.

PROCEDURE

An internal standard stock solution of final concentration 40 mg/liter is made up by weighing 1-methyl-5-mercaptotetrazole and diluting to volume with mobile phase.

The sample is weighed (about 5 mg) and diluted with internal standard stock solution to obtain a final concentration of 5 mg/50 ml.

Approximate retention times (min.):
1-methyl-5-mercaptotetrazole: 8
1-carboxymethyl-5-mercaptotetraxole: 11

CALCULATIONS

Percentages are determined by peak height.
This invention is capable of industrial application.
We claim:

1. The process for the production of an alkaline solution of 5-mercaptotetrazolyl-1-acetic acid which consists of the consecutive steps of
   (a) heating at a temperature between 50° C. and 100° C. a solution in chloroform or carbon tetrachloride of tetrazolyl-1-acetic acid with enough added acetic acid to bring the tetrazolyl-1-acetic acid into solution and twice as many moles of bromine as of tetrazolyl-1-acetic acid to produce 5-bromotetrazolyl-1-acetic acid,
   (b) precipitating said 5-bromotetrazolyl-1-acetic acid as a solid by addition of a nonsolvent therefor which is a liquid alkane or a mixture of liquid alkanes,
   (c) recovering said solid 5-bromotetrazolyl-1-acetic acid and heating it to reflux in a lower aliphatic alcohol in the presence of an amount of thiourea which is equimolar to the 5-bromotetrazolyl-1-acetic acid and then
   (d) mixing with the resulting mixture dilute, aqueous sodium hydroxide or potassium hydroxide with stirring at room temperature to produce an alkaline solution of 5-mercaptotetrazolyl-1-acetic acid.

* * * * *